United States Patent [19]

Gadelius

[11] Patent Number: 5,429,121
[45] Date of Patent: Jul. 4, 1995

[54] SURGICAL RETRACTOR

[75] Inventor: Gustaf Gadelius, Stockholm, Sweden

[73] Assignee: Per Jettman, Stockholm, Sweden

[21] Appl. No.: 108,603

[22] PCT Filed: Mar. 17, 1992

[86] PCT No.: PCT/SE92/00163
§ 371 Date: Aug. 25, 1993
§ 102(e) Date: Aug. 25, 1993

[87] PCT Pub. No.: WO92/16151
PCT Pub. Date: Oct. 1, 1992

[30] Foreign Application Priority Data

Mar. 20, 1991 [SE] Sweden ................... 9100845

[51] Int. Cl.⁶ .......................................... A61B 17/02
[52] U.S. Cl. ................... 600/217; 403/107; 403/232.1
[58] Field of Search ............... 128/20, 17, 18; 606/191, 198; 604/106; D24/135; 403/107, 106, 104, 103, 232.1, 233, 234; 269/190, 219, 264

[56] References Cited

U.S. PATENT DOCUMENTS

| 1,947,649 | 2/1934 | Kadavy . | |
|---|---|---|---|
| 2,850,008 | 9/1958 | Resch | 128/20 |
| 3,750,652 | 8/1973 | Sherwin | 128/20 X |
| 3,840,014 | 10/1974 | Ling et al. . | |
| 4,263,899 | 4/1981 | Burgin | 128/20 X |
| 4,502,485 | 3/1985 | Burgin | 128/20 X |
| 4,754,746 | 7/1988 | Cox | 128/20 |

FOREIGN PATENT DOCUMENTS

| 2080113 | 2/1982 | United Kingdom | 128/20 |
|---|---|---|---|
| 2218912 | 11/1989 | United Kingdom . | |
| 0908342 | 2/1982 | U.S.S.R. | 606/198 |
| WO8905131 | 6/1989 | WIPO . | |
| 9218055 | 10/1992 | WIPO | 128/20 |

OTHER PUBLICATIONS

The Lewton Company, "Surgical Instrument Catalog", New Jersey 1970, p. 117 (Kocher Goitre Retractor, No. A 12-0430, Kifa).

Primary Examiner—Richard J. Apley
Assistant Examiner—Donna L. Maraglio
Attorney, Agent, or Firm—Young & Thompson

[57] ABSTRACT

An openable retractor for use in an operation wound-/surgical incision in the region of a patient's spine. The retractor includes two mutually-hinged halves (2, 4), each of which comprises an upper hinge part (6, 6') which, on the side thereof remote from the hinge, merges with a downwardly-extending shaft (8) at a radial distance from the hinge axis or its extension, a wound widening and restraining part (10) which projects laterally from the lower part of the shaft in a direction away from the hinge axis and which is intended for engagement with muscle tissue on one side of the operation wound, and a latching device (68) which is intended to be applied in the region of the hinge formed by the hinge parts (6, 6') of respective retractor halves and which functions to lock the retractor halves in an outwardly angled active position (functional position).

17 Claims, 4 Drawing Sheets

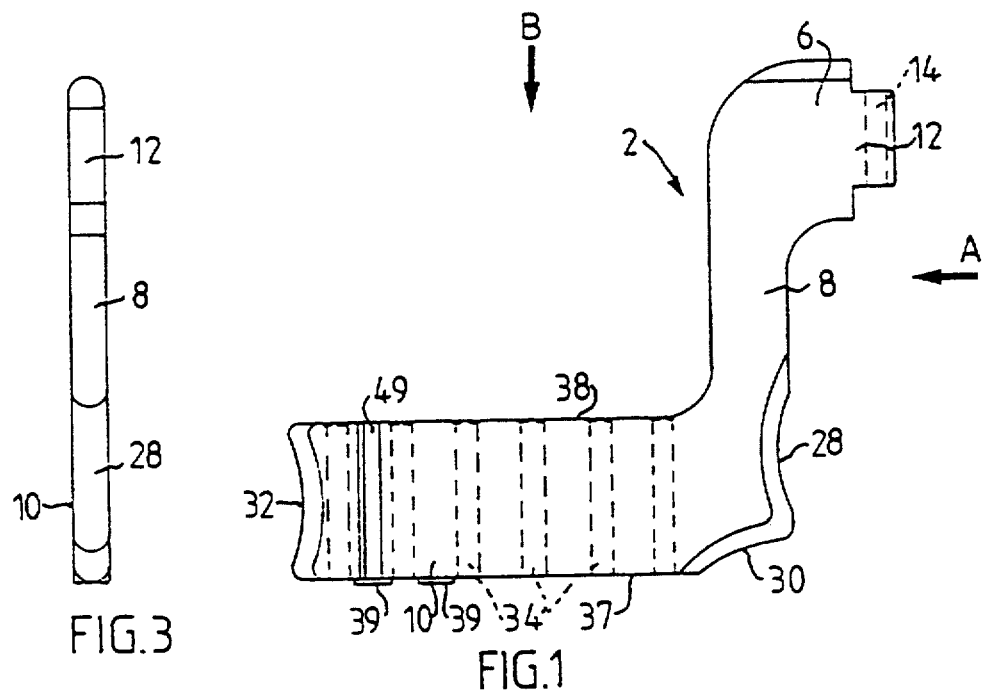
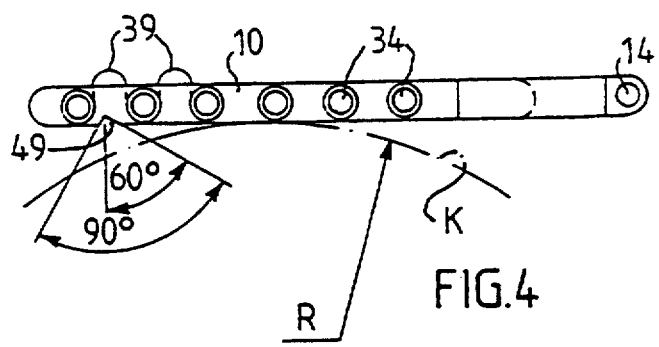

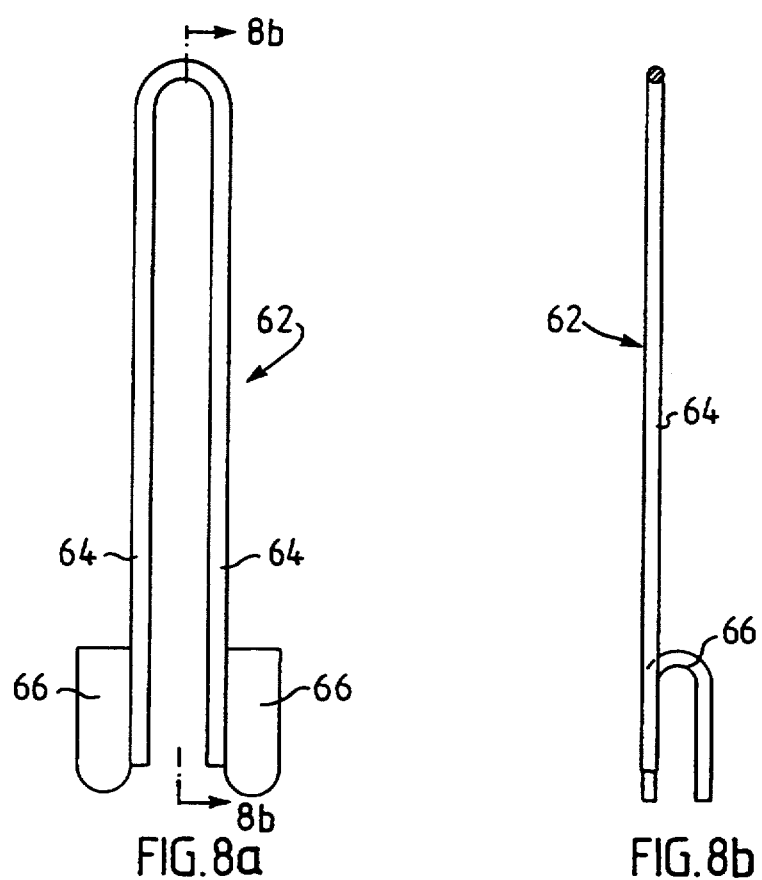

5,429,121

SURGICAL RETRACTOR

TECHNICAL FIELD

The present invention relates to a widenable surgical retractor, and particularly, but not exclusively, to a retractor which is intended for use in holding tissue, etc., away from the field of operation in operation wounds/surgical incisions in the region of a patient's spine, said retractor including two mutually-connected retractor halves.

The invention thus relates to a widenable, more particularly an angularly extendable retractor by means of which tissue, etc., can be held away from the field of operation, and then particularly from the field of an operation wound in the region of a patient's spine.

In certain types of spine operations, for instance operations for prolapsed discs or fractures of the vertebrae, it is necessary for the surgeon to be able to reach particular vertebrae and intermediate cartilage discs with the surgical instruments needed to carry out the operation. In order to make this possible, both the subcutaneous fascia and the muscular tissue which lies beneath or inwardly of the fascia must be held to one side in the region of the operation wound, so that the wound can be held open and thereby provide access to the vertebrae.

BACKGROUND ART

The type of retractor normally used at present includes a pair of mutually separable tissue-restraining plates or wings. The retractor is first inserted into the operation wound, often in the form of an incision, with the restraining plates lying contiguous with one another, such that the outer surfaces of the plates are in abutment with the mutually-opposing "walls" of the incision, whereafter the plates are forced apart sufficiently for the field of operation to be at least slightly accessible to the surgeon.

However, the restraining wings or plates of the known retractor, which bear against the walls of an operation wound and function to hold the wound open have a vertical extension such that the plates extend from the bottom of the wound up to the surface of the surrounding skin, even when the operation wound/incision is relatively deep. Thus, the vertical extension of the retractor plates covers the walls of the operation wound over the whole of their depth, including the uppermost layer of skin and associated fascia.

One problem in this regard, however, is that the fascia is far less elastic than the inwardly-lying muscular tissue, and consequently the separating force which the retractor needs to exert between the walls of the operation wound (when the retractor is adjusted to its wound widening and restraining state) is determined primarily by the smaller elastic resistance of the fascia. It has also been found that a retractor whose restraining plates have the aforesaid vertical dimensions has a pronounced tendency to slide upwards and out of the operation wound as a result of tension in the fascia. This tendency is, of course, particularly problematic during the course of an operation, since it necessitates repeated adjustment of the position of the retractor. Furthermore, due to the structural design of this known retractor, with mutually parallel and mutually separable wound-opening and wound-restraining plates, this known retractor causes muscular atrophy as a result of the high surface abutment pressure which prevails between muscle and the respective vertical front and rear edges of the restraining plates, this abutment being essentially a line contact between said edge and said muscle.

Another problem, which is closely related to the conditions which prevail in an operation in which the surgical section or wound area lies in the region of the patient's spine is that the spine vertebrae have projections (spinous and transverse spinelike processes) which are seated on the vertebrae arch, which in turn is seated on the body of vertebrae.

The retractor should therefore be constructed so as to provide sufficient space not only for the spine-vertebrae but also for the spinal vertebrae arches with the spinous and transverse spinelike processes of the vertebrae.

THE OBJECT OF THE INVENTION

The object of the present invention is to provide a novel type of openable, hinged retractor which is capable of solving the aforesaid problems.

DISCLOSURE OF THE INVENTION

This object is mainly achieved in that each of the retractor halves, which are pivotally connected together for relative movement in a scissor-like fashion, comprises a hinge part which on the side thereof which faces away from the hinge merges with a downwardly-extending shaft at a radial distance from the hinge axis or from the extension of said axis, a wound widening and wound-restraining part which projects laterally away from the hinge axis and which is intended to be placed against the muscle tissue on one side of the operation wound, a latching means which is intended to be placed in the region of the hinge formed by the hinge-parts of respective retractor halves such as to mutually latch said halves in an outwardly angled active position (functional position).

A retractor of this construction enables the wound widening and wound-restraining parts of the retractor to be placed in the operation wound so as to act primarily on the muscular tissue beneath (inwardly of) the overlying fascia. Thus, the problem caused by the retractor sliding up out of the operation wound is avoided, because the wound-restraining parts of the retractor are located beneath the fascia.

Further developments and preferred embodiments of the invention are defined in the depending claims.

According to one practical embodiment of the invention, the wound widening and restraining parts of the retractor have a generally constant vertical extension within the greater part of their longitudinal extension and are curved in mutually opposite directions, with the concave inner surfaces facing towards each other, wherein each of the centers of curvature of a respective curve preferably lies along a respective axis which extends generally parallel with the hinge axis.

According to another preferred embodiment of the invention, the free outer edges of the wound widening and restraining parts of the retractor remote from the shaft are inwardly concave so as to increase the functional pressure on the muscle tissue against which said parts engage in their angularly-extended positions.

Since the inventive retractor is intended to be used so that the aforesaid retractor parts will normally engage muscle tissue with the fascia and associated skin layer lying above the upper defining edge of said parts, it may be necessary to provide separate means for supporting the fascia and the fat layers of the skin, these means being removably insertable into the upper part of the wound widening and restraining retractor parts.

In addition, each said part may suitably be provided with mutually spaced and mutually parallel attachment holes for accommodating insertable support elements which function to form an edge support (for skin layers and fascia) in the region above the upper defining edge of the wound widening and restraining part, said attachment holes extending generally parallel with the shaft of the retractor halves and/or the hinge axis.

This support element may, for instance, have the form of a U-shaped metal device whose legs (preferably parallel legs) can be inserted into the attachment holes in respective wound widening and restraining parts of the retractor.

BRIEF DESCRIPTION OF THE DRAWINGS

The invention will now be described in more detail with reference to a number of exemplifying embodiments of the structural components of an inventive retractor, and with reference to the accompanying drawings, in which FIG. 1 and FIG. 2 are side views of a respective retractor half which when hingedly-connected are able to angle outwardly, in a scissor-like fashion, and which form the inventive retractor; FIG. 3 illustrates the retractor half shown in FIG. 1, seen in the direction of the arrow A; FIG. 4 illustrates the same retractor half seen in the direction of the arrow B; FIG. 8a is a front view and FIG. 8b a sectional view (taken on the line 8b—8b in FIG. 8a) of a third type of support element.

EMBODIMENTS OF THE INVENTION

Figure 2:
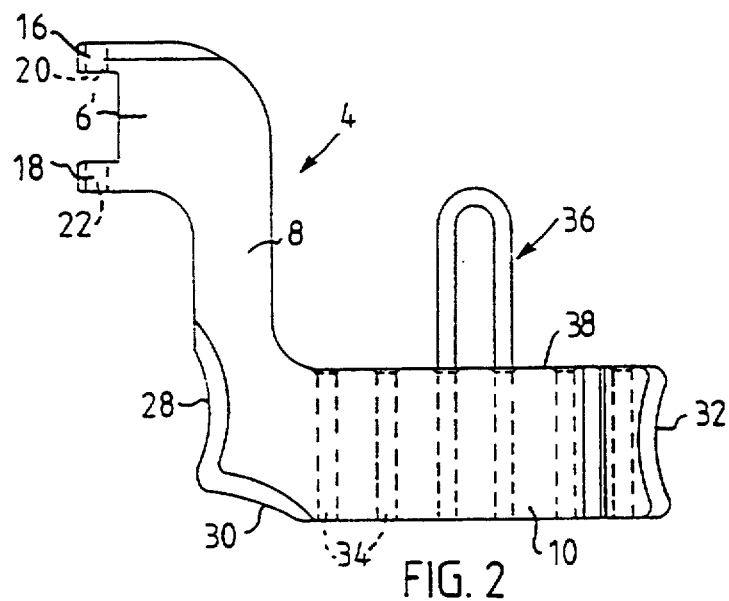

Reference is first made to FIG. 1 and FIG. 2, which each illustrate a respective half 2 and 4 of the inventive retractor whose active parts can be angled outwardly relative to one another, in a scissor-like fashion. Each retractor half includes three main parts, i.e. respective hinge parts 6 and 6' which merge downwardly with a depending shaft 8. A wound widening and restraining part 10 extends outwardly from the lower part of the shaft 8 in a direction opposite to respective hinge parts 6, 6', said wound widening and restraining part 10 hereinafter being simply referred to as restraining part. As shown in FIG. 1, the hinge part 6 has an outwardly-projecting shoulder 12, which is provided with a penetrating hole 14, whereas the hinge part 6', shown in FIG. 2, has a fork-like structure which includes two legs 16, 18, with mutually coaxial penetrating holes 20, 22. In the assembled state of the inventive retractor, the two hinge parts 6, 6' are positioned so that the three holes 20, 14, 22 are mutually in register and can receive a common hinge pin (not shown).

As illustrated in FIGS. 1-4, the retractor halves 2, 4 have a generally constant thickness in the hinge part, the shaft and restraining part. The retractor halves are preferably made of metal, for instance stainless steel, although the retractor halves may, alternatively, be made of a suitable plastic material, such as a reinforced fiber plastic. As will be seen from the drawings, the two restraining retractor parts 10 have a substantially constant height or vertical extension.

Figure 6:
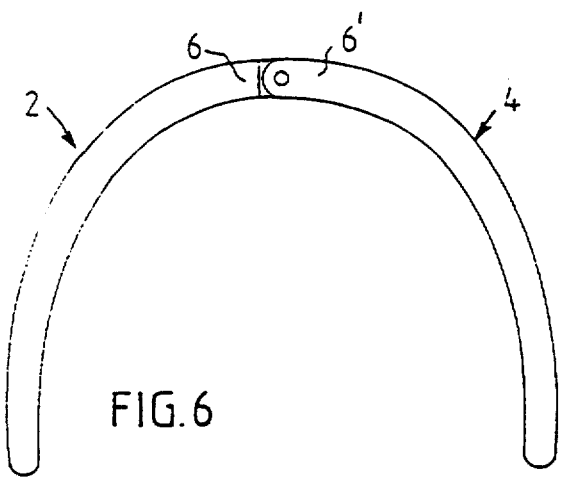
FIG. 6 illustrates a retractor from above, with the retractor halves swung outwards (mutually separated)

As illustrated in FIGS. 1-4, in the initial stages of manufacture, the retractor halves have a flat shape, and the restraining parts are subsequently curved in mutually opposite directions prior to joining the retractor halves together, through the medium of their respective hinge parts 6, 6'. The curvature of said restraining parts is indicated by the chain line K in FIG. 4, where the radius of curvature is referenced R. The two restraining retractor parts are curved so that their respective concave inner surfaces 24, 26 (see FIG. 6) face towards one another. In practice, the radius of curvature R of said wound restraining parts will preferably lie in the range of 50-70 mm, and may suitably be about 60 mm.

Formed in the lower part of the shaft 8 are concave recesses 28, 30, whose radius of curvature is suitably in the order of 15-35 mm, preferably about 25 mm.

The free outer edges of the restraining parts 10 remote from the shaft are provided with inwardly concave recesses, as illustrated by the outer contour line 32 in FIG. 1. The radius of curvature of this concave recess 32 is in the order of 15-35 mm, preferably about 25 mm.

Each restraining part 10 has provided therein a number of mutually-spaced and mutually-parallel attachment holes 34 into which support elements 36 can be inserted. These support elements are intended to form edge supports (primarily for skin layers and fascia) in the region above the upper-defining edge 38 of a respective restraining part.

In accordance with one preferred, particularly simple embodiment, the support element 36 may suitably have the shape of an inverse-U, as shown in FIG. 2. In this case, the support element has the form of a metal wire that has been bent to a U-shape. The two legs of the U-shaped support are inserted into a pair of attachment holes 34, in the manner shown. Disc-like hooks or barbs 39 which project out from the convex side of the part 10 of the retractor may be provided on the underside 37 of said restraining part 10 and there form additional muscle engaging means which assist in preventing the retractor from sliding up out of the operation wound.

Figure 5A:
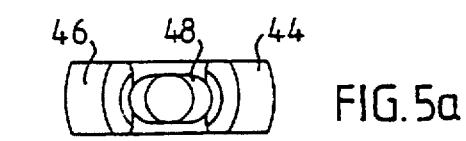
FIG. 5a is an end view of the latching device.
Figure 5B:
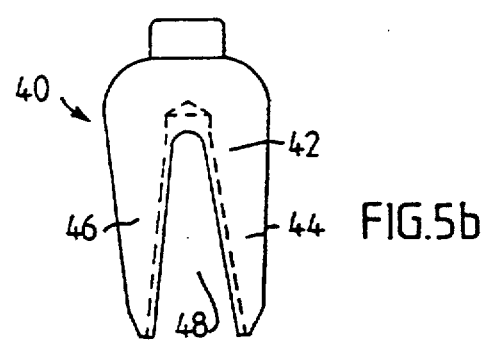
FIG. 5b is a side view of a latching device for an inventive retractor.

FIGS. 5 and 5a illustrates an exemplifying embodiment of latching means whereby the retractor halves 2, 4 can be locked mutually in an outwardly angled, active position or functional position. In this case, the latching means 40 is a latching element which is intended to straddle the hinge formed by the pivotally-connected hinge parts 6, 6'. In the case of the illustrated embodiment, this latching element is a U-shaped metallic element 42 whose legs 44, 46 define therebetween a V-shaped space 48 which enables the latching element 40 to be placed lockingly over the hinge from above. Naturally, the latching means may have many other alternative forms. The one essential feature of the latching means is that it can be placed easily in position in the region of the hinge, and that it will positively lock the two retractor halves 2, 4 in relation to one another when the latching means is brought to its locking position.

The wound-restraining parts 10 may be provided conveniently with engagement slots or grooves 49 on their respective concave inner surfaces, as shown in FIGS. 1 and 4. These slots or grooves are intended to form anti-slipping engagement locations for, e.g., the legs of an instrument used to open (angle outwardly) the wound widening and restraining parts of the inventive retractor to the desired extent, wherein the retractor is then locked in position by applying the aforesaid latching means 40, i.e. the latching element or stirrup 42 in the case of the illustrated embodiment.

Figure 7:
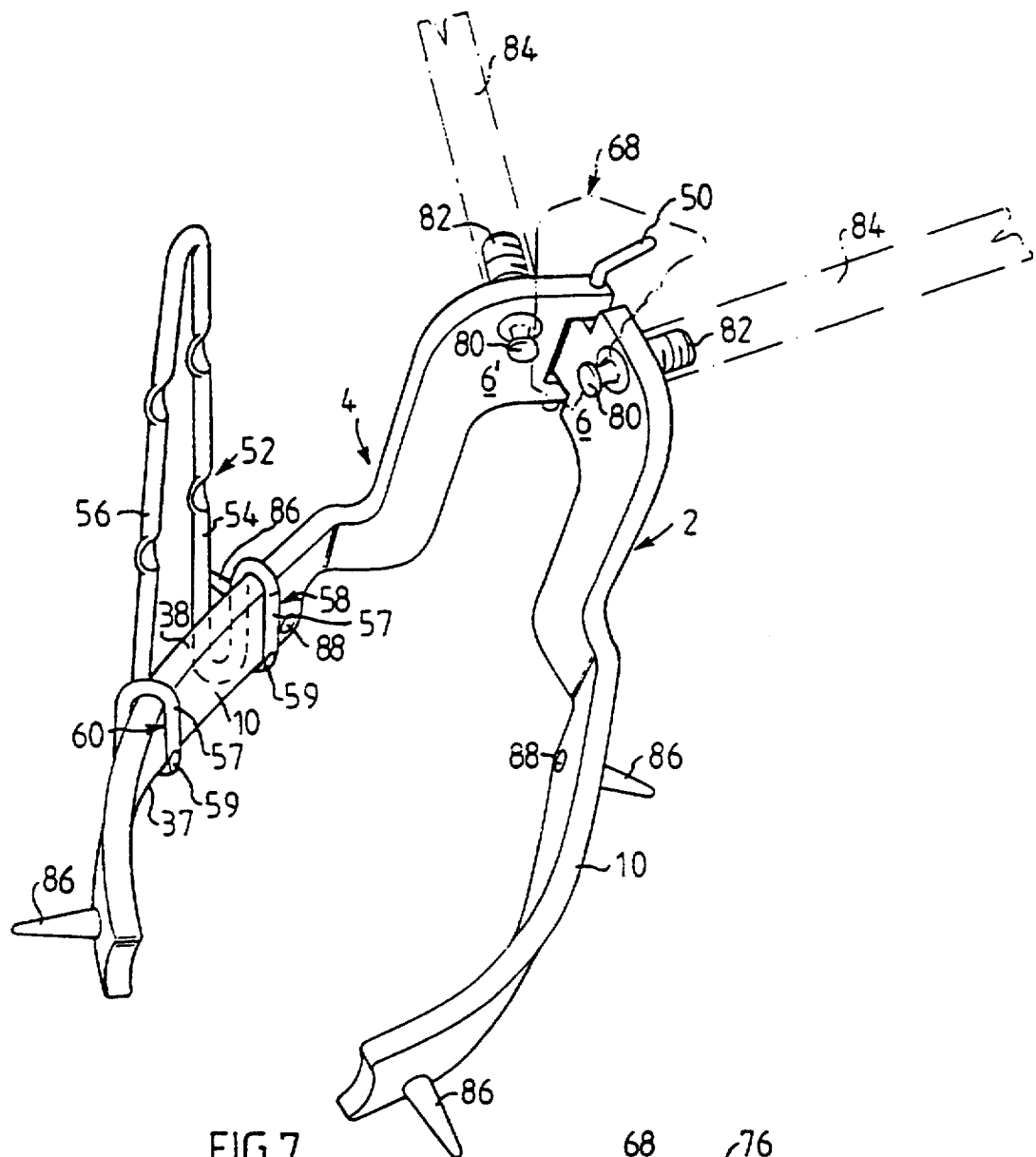
FIG. 7 is a perspective view of a slightly different embodiment of a complete retractor according to the invention, in which the latching means is different to that of the FIG. 5 embodiment and in which the support element is different to that of the FIG. 2 embodiment.

The two halves 2, 4 of the embodiment of the inventive retractor illustrated in FIG. 7 are hingedly connected at the hinge parts 6, 6' by means of an L-shaped hinge pin 50, through the holes 20, 14, 22. The illustrated retractor half 4 is provided with a support element 52 which is detachably fitted to the restraining part 10 by means of attachment parts 58, 60 each of which is located at the lower part of a respective leg 54, 56 of the support element, these attachment parts being fitted over the restraining part from above, so as to straddle said part. In the illustrated embodiment, the support element 52 has the form of a U-shaped wire element, or wire stirrup, wherein that part of the stirrup-like element which lies above the defining edge 38 has generally the form of an inverse V. The downwardly directed end parts 57 of the attachment parts 58, 60 have inwardly directed abutment portions 59 which hook firmly against the edge of the underside 37.

FIGS. 8a and 8b are respectively front and side views of an alternative form of a support element 62, which includes a U-shaped wire stirrup like element 62, which has two legs 64. Provided on the lower parts of the legs 64 are saddle-like attachment parts 66. The support element 62 is fitted onto the relevant restraining part 10, by placing the two attachment parts 66 of the support element over the edge 38 of the restraining part 10 so as to straddle said edge.

Figure 9:
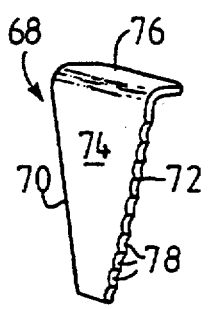
FIG. 9 is a perspective view of the latching means used in the FIG. 7 embodiment.

In the embodiment illustrated in FIG. 7, the latching means is a disk shaped latching element 68 which has mutually converging side edges 70 and 72 on the active locking-wedge part 74. As will be seen from FIG. 9, this locking-wedge part 74 is provided at the top thereof with an angled gripping part 76. The latching element is shown in FIG. 7 solely in chain contour. Formed in the side edge 72 is a series of arcuate recesses or notches 78 which give the edge a sawtooth-like configuration. When in its functional position, the latching element 68 coacts with an outwardly widened projection 80 on the inside of the upper hinge parts 6, 6' of the retractor halves 2, 4. When in its downwardly inserted latching position between the projections 80, the latching element 68 is fixed wedgedly by virtue of the engagement of one of its edge recesses 78 with the adjacent projection 80.

Although the projections 80 may be attached to the inner surfaces of the hinge parts 6, 6' in any desired manner, it is preferred that each projection 80 is comprised of the end part of an externally threaded fastener pin which has threaded portion 82 that is screwed into a penetrating threaded hole in a respective hinge part 6, 6', this latter alternative affording a particularly rational solution. The threaded portion 82 of the fastener pin projects out from the hinge part on the outer side thereof and therewith forms a screw-threaded pin attachment for coaction with the internally screw-threaded end of a tubular shaft 84, which is shown in chain contour in FIG. 7.

The other hinge part also has a fastener pin which is provided with a similar projection 80 and with a similar screw-threaded part 82 which coacts with a corresponding tubular shaft 84. The two tubular shafts 84, 84 together form a practical device for manually separating, or manually swinging apart, the two retractor halves 2,4 to a desired angular position, said halves then being fixed in this position by inserting the latching element 68 down between the projections 80.

There is suitably provided close to the lower edge of the restraining parts 10 of the retractor halves 2, 4 one or more outstanding pins 86, on the curved, convex outer surfaces of said parts 10. These pins, or points, 86 form muscle engaging means which assist in preventing the retractor from sliding up out of the operation wound. The pins 86 thus form an alternative to the hooked barbs 39 of the embodiment illustrated in FIGS. 1 and 4. Although the pins 86 may be attached to the restraining parts 10 in any appropriate manner, in practice said pins will preferably be comprised of the outwardly directed point of a pin means which has a rear, externally screw-threaded attachment part 88 which is screwed into a screw-threaded penetrating hole located in the near vicinity of the lower edge of respective restraining parts 10.

I claim:

1. An openable surgical retractor, for use with operation wounds or surgical incisions in the region of a patient's spine, said retractor comprising:
   two retractor halves pivotally interconnected by a hinge means about a hinge axis, wherein each retractor half comprises an upper hinge part, an elongate shaft member having a proximal end and a distal end, and a wound widening and restraining part, wherein said upper hinge part merges on one edge thereof with said hinge means and on another edge thereof with said proximal end of said shaft member, said elongate shaft member extending downwardly from said upper hinge part along an axis substantially parallel to said hinge axis, said wound widening and restraining part being elongated and projecting substantially perpendicularly from said distal end of said shaft member in a direction away from said hinge axis and terminating in a free distal end remote from said shaft member; and
   a latching means for locking said retractor halves in an outwardly angled functional position, said latching means fitting between said upper hinge parts adjacent said hinge means, whereby each retractor half is capable of sideways restraining engagement with muscle tissue on one side of an operation wound.

2. A retractor according to claim 1, wherein the thickness of the retractor halves is generally constant in the hinge parts, the shafts and the wound widening and restraining parts.

3. A retractor according to claim 1, wherein the wound widening and restraining parts have a generally constant height at least within a substantial part of their length; said wound widening and restraining parts being curved in mutually opposite directions with concave inner surfaces of said parts facing towards each other; and wherein each center of curvature of a respective concave inner surface lies along a respective axis which extends generally parallel with the hinge axis.

4. A retractor according to claim 3, wherein the radius of curvature of each wound widening and restraining parts lies in the range of 50–70 mm.

5. A retractor according to claim 1, wherein the distal end of each said shaft includes a first arcuate recess on an edge remote from said wound widening and restraining part and a second arcuate recess on an edge adjacent said wound widening and restraining part; each of said first and second arcuate recesses having a radius of curvature in the range of 15–35 min.

6. A retractor according to claim 1, wherein the free distal ends of the wound widening and restraining parts remote from the shafts are inwardly concave and have a radius of curvature in the range of 15–35 mm.

7. A retractor according to claim 1, wherein each wound widening and restraining part includes a plurality of mutually-spaced and mutually-parallel attachment holes for the insertion of support elements which function to form an edge support for skin layers and fascia in a region above an upper edge of a wound widening part; said attachment holes extending generally parallel with said hinge axis.

8. A retractor according to claim 7, further including a plurality of support elements each having the form of an inverse U-shaped metal element and two legs which can be inserted into the attachment holes.

9. A retractor according to claim 1, further including at least one outstanding pin located on the outside of each restraining part, said at least one outstanding pin functioning as anchoring means in the muscle tissue in an outwardly lying part of an operation wound in which the retractor is used.

10. A retractor according to claim 1, wherein the latching means has the form of a latching element which is intended to be straddled over the hinge means; said latching element being in the form of a U-shaped or V-shaped metallic element and having legs with free extremities; and said legs of said metallic element defining a space whose width increases in a direction towards the free extremities.

11. An openable surgical retractor, for use with operation wounds or surgical incisions in the region of a patient's spine, said retractor comprising two retractor halves pivotally interconnected by hinge means defining a hinge axis, wherein each retractor half comprises an upper hinge part which merges at the bottom thereof, on a side remote from said hinge means, with a downwardly-extending shaft member at a radial distance from the hinge axis or its extension, a wound widening and restraining part which projects laterally from a lower part of the shaft member in a direction away from said hinge axis and which is intended for engagement with muscle tissue on one side of the operation wound; each restraining part carrying at least one upwardly directed support element which functions as a tissue edge support to hold to one side skin layers and fascia in the region above an upper edge of said restraining part, each said supporting element having at its lower part at least one attachment part adapted to be placed over the restraining part from above so as to straddle said restraining part, thereby enabling the support element to be detachably fitted to the restraining part, and a latching means intended to be fitted on to the retractor in a region of the hinge means formed by the upper hinge parts of said two retractor halves, in a manner to lock said halves in an outwardly angled functional position for sideways restraining engagement with muscle tissue.

12. A retractor according to claim 11, wherein the support element is a wire structure that has two legs and is in the form of an inverted U or V; and at least one of the two legs of the structure supports at its lower part the attachment part of said support element.

13. A retractor according to claim 12, wherein each of the two legs of the wire structure includes an attachment part.

14. A retractor according to claim 13, wherein the attachment part comprises of a strip element which has been bent to a U-shaped cross-section and which is firmly attached along an edge region thereof to the lower part of the leg.

15. A retractor according to claim 12, wherein a bottom part of each of said two legs of the wire structure is formed as an attachment part which includes an upwardly directed, curved wire section extending from the lowermost part of the leg, said wire section being curved downwards at the top thereof and terminating in a downwardly directed end part which has a lower free end having a hooked abutment part for engagement with a lower edge of the restraining part.

16. An openable surgical retractor, for use with operation wounds or surgical incisions in the region of a patient's spine, said retractor comprising two retractor halves pivotally interconnected by hinge means defining a hinge axis, wherein each retractor half comprises an upper hinge part which merges at the bottom thereof, on a side remote from said hinge means, with a downwardly-extending shaft member at a radial distance from the hinge axis or its extension, a wound widening and restraining part which projects laterally from a lower part of the shaft member in a direction away from said hinge axis and which is intended for engagement with muscle tissue on one side of the operation wound; a latching means intended to be fitted on to the retractor in a region of the hinge means formed by the upper hinge parts of said two retractor halves, in a manner to lock said halves in an outwardly angled functional position for sideways restraining engagement with muscle tissue, said latching means comprising a disc element having a pair of mutually converging side edges, at least one of said side edges including a series of arcuate recesses or notches; each of the retractor halves having on the inside of its upper hinge part an outwardly widened projection; and said disc element adapted to be inserted down between each projection to a latching position in which the disc element is fixed wedgingly between the projections, with one of the arcuate recesses or notches in engagement with the contacting projection.

17. A retractor according to claim 16, wherein each projection is formed by one end part of an externally screw-threaded fastener pin which is screwed into a screw-threaded hole on the hinge part, wherein each said fastener pin projects out from the hinge part on that side of the hinge part which is opposite to said projection; and said screw-threaded fastener pin forming a screw attachment for a tubular shaft which has an internal screw-thread at one end thereof and which together with a corresponding tubular shaft on the other retractor half can be used to separate or swing apart the retractor halves to the functional position.

* * * * *